(12) United States Patent
Biesecker (10) Patent No.: US 7,204,959 B2
(45) Date of Patent: Apr. 17, 2007

(54) STABILIZED POWDERED FORMALDEHYDE

(76) Inventor: James L. Biesecker, 8510 Cedarhome Dr. NW., Stanwood, WA (US) 98292

( * ) Notice: Subject to any disclaimer, the term of this patent is extended or adjusted under 35 U.S.C. 154(b) by 346 days.

(21) Appl. No.: 10/357,596

(22) Filed: Feb. 4, 2003

(65) Prior Publication Data

US 2003/0229170 A1    Dec. 11, 2003

Related U.S. Application Data

(60) Provisional application No. 60/355,730, filed on Feb. 5, 2002.

(51) Int. Cl.
*A01N 1/00*    (2006.01)
(52) U.S. Cl. ............................ 422/61; 436/128; 424/75
(58) Field of Classification Search ................. 422/61; 436/128; 424/75
See application file for complete search history.

(56) References Cited

U.S. PATENT DOCUMENTS 3,653,499 A * 4/1972 Richter ........................ 206/568
3,888,989 A   6/1975 Blaszczak ..................... 424/280
6,031,064 A   2/2000 Guenther et al. ............. 528/254

OTHER PUBLICATIONS

J. Frederic Walker, Formaldehyde (Reinhold Publishing Corporation, Third Edition 1964).

* cited by examiner

*Primary Examiner*—Monique T. Cole
(74) *Attorney, Agent, or Firm*—Christensen O'Connor Johnson Kindness PLLC (57) ABSTRACT

According to an aspect of the invention, a polymerized form of formaldehyde is available in granular form containing a polymerized form of formaldehyde, such as paraformaldehyde, a buffer, such as sodium phosphate dibasic anhydrous, and a stabilizer, such as hydroxymethyl cellulose, or hydroxypropyl methyl cellulose. When added to an aqueous solvent, the paraformaldehyde can dissolve in alkaline solution, and depolymerizes into a formaldehyde solution containing a stabilizer. Optionally a second member of the buffer pair or another buffer or pH adjuster can be used The stabilized depolymerized formaldehyde solution is then ready for use, or can be modified by addition of other substances, such as sodium phosphate monobasic monohydrate. Additionally, an additional buffer may be included in the granular mixture to increase the rate at which the solid dissolves and depolymerizes.

15 Claims, 4 Drawing Sheets

|  | Type Formula | Approximate Range of Polymerization ($n$) | $CH_2O$ Content (% by Weight) | Melting Range (°C) | Solubility* | | | |
|---|---|---|---|---|---|---|---|---|
|  |  |  |  |  | Acetone | Water | Dilute Alkali | Dilute Acid |
| I. Linear Polymers (On vaporization these depolymerize to monomeric formaldehyde gas) |  |  |  |  |  |  |  |  |
| Lower polyoxymethylene glycols | $HO(CH_2O)_n \cdot H$ | 2-8 | 77-93 | 80-120 | s-i | vs | vs | vs |
| Paraformaldehyde | $HO(CH_2O)_n \cdot H$ | 6-100 | 91-99 | 120-170 | s-i | ds | s | s |
| Alpha-polyoxymethylene | $HO(CH_2O)_n \cdot H$ | 100-300 | 99.0-99.9 | 170-180 | i | vds | s | s |
| Beta-polyoxymethylene | $HO(CH_2O)_n \cdot H + H_2SO_4$ (trace) | 100-300 | 98-99 | 165-170 | i | vds | ds | ds |

| Key | |
|---|---|
| s | soluble |
| i | insoluble |
| vs | very soluble |
| vds | very difficulty soluble |
| ds | difficultly soluble |

|  | Type Formula | Approximate Range of Polymerization (n) | CH$_2$O Content (% by Weight) | Melting Range (°C) | Solubility* | | | |
|---|---|---|---|---|---|---|---|---|
|  |  |  |  |  | Acetone | Water | Dilute Alkali | Dilute Acid |
| I. Linear Polymers (On vaporization these depolymerize to monomeric formaldehyde gas) |  |  |  |  |  |  |  |  |
| Lower polyoxymethylene glycols | HO(CH$_2$O)$_n$•H | 2-8 | 77-93 | 80-120 | s-i | vs | vs | vs |
| Paraformaldehyde | HO(CH$_2$O)$_n$•H | 6-100 | 91-99 | 120-170 | s-i | ds | s | s |
| Alpha-polyoxymethylene | HO(CH$_2$O)$_n$•H | 100-300 | 99.0-99.9 | 170-180 | i | vds | s | s |
| Beta-polyoxymethylene | HO(CH$_2$O)$_n$•H + H$_2$SO$_4$ (trace) | 100-300 | 98-99 | 165-170 | i | vds | ds | ds |

| Key | |
|---|---|
| s | soluble |
| i | insoluble |
| vs | very soluble |
| vds | very difficulty soluble |
| ds | difficultly soluble |

FIGURE 1

Effect of pH on solubility of paraformaldehyde. (From Löbering, J., Ber., 69, 1846 (1936).

FIGURE 2

Effect of pH on paraformaldehyde solubility constant. (From Löbering, J., Ber., 69, 1846 (1936).

STABILIZED POWDERED FORMALDEHYDE

RELATED APPLICATION

This application claims priority under 35 U.S.C. §119 to U.S. Provisional patent application Ser. No. 60/355,730, filed Feb. 5, 2002, incorporated herein fully by reference.

FIELD OF THE INVENTION

The present invention is related to powdered formalin for uses in the fields of histology, particularly fixatives used in clinical and histology laboratories, and of chemistry, including the production of plastics and polymerized forms of aldehydes, and more particularly to a powdered forms, and to methods for their manufacture and use.

BACKGROUND

Aldehyde solutions are produced and used for a wide variety of purposes. For example, formaldehyde ($CH_2O$) is a widely manufactured and transported chemical for use as a fixative in clinical and histology laboratories. Formaldehyde may be purchased and delivered as a 37% liquid solution with approximately 12% to approximately 15% methanol added. This product may then be diluted, often in water, to an approximately 3.7% solution for fixation purposes, such as fixation of tissue. Typically, a fixative is used to preserve biological specimens such as biopsy or tissue specimens, for medical diagnosis.

Additionally, formaldehyde may be produced in a concentrated liquid form for producing a variety of polymers and resins. These polymers and resins may include linear polymers, lower polyoxymethylene glycols, paraformaldehyde, alpha-polyoxymethylene, beta-polyoxymethylene, polyoxymethylene glycol derivatives, polyoxymethylene diacetates, polyoxymethylene dimethyl ethers, gamma-polyoxymethylene, delta-polyoxymethylene, epsilon-polyoxymethylene, high molecular weight polyoxymethylenes, aceteal resins, cyclic polymers, and tetraoxane.

Formaldehyde solutions may be produced by heating solid formaldehyde polymers with water. Using a heating technique, formaldehyde solutions above 50% by weight of formaldehyde can be obtained from solid formaldehyde polymers. Concentrations of liquid formaldehyde above about 50% precipitate at about "room temperature" (approximately 25° Celsius) as polymers of formaldehyde. The temperature necessary to maintain a clear solution and prevent separation of solid polymer increases from room temperature to about 100° Fahrenheit as the solution concentration is increased to about 37%.

Additionally, there are several other disadvantages to the process of diluting and storing formaldehyde in liquid form.

Processes for making formaldehyde solutions are hazardous and difficult to perform.

Processes for making formaldehyde solutions often require specialized equipment which is often not available to clinical or histology laboratories. For example, in liquid form there has to be adequate ventilation with protective mechanisms to prevent inhalation of vapors.

Additionally, 37% formaldehyde solutions must be stored at no lower than room temperature conditions, otherwise the solutions can lose effectiveness and become unstable if stored for an extended period of time.

Processes of producing and storing other aldehyde solutions often exhibit similar difficulties and disadvantages.

There are also several other disadvantages to the process of heating formaldehyde polymers to generate formaldehyde solutions.

Processes for producing and storing aldehyde solutions are hazardous and difficult to perform.

Processes for producing and storing aldehyde solutions often require specialized equipment which is often not readily available. For example, in liquid form there has to be adequate ventilation with protective mechanisms to prevent inhalation of vapors.

As a result of the above disadvantages, currently liquid aldehyde solutions are frequently produced at a manufacturing facility and then transported to an end user. However, transporting liquid aldehyde solutions is expensive and dangerous. Containers are large, heavy and may rupture during transport thereby exposing other individuals to the dangerous solution.

Accordingly, an easier, safer technique for producing, storing and transporting aldehydes, such as formaldehyde, for a variety of purposes is desirable.

SUMMARY

According to an aspect of the invention, a polymerized form of aldehyde or other fixative is available in granular form containing a polymerized form of the fixative and at least one buffer, such as a basic component of a buffer pair. When added to an aqueous solvent, the polymerized fixative dissolves thereby forming a solution of the fixative. The solution is then ready for use, or can be modified by addition of other substances. For example, a stabilizer may be added.

According to another aspect of the invention, a composition contains a granular form of formaldehyde, such as paraformaldehyde, a buffer, such as sodium phosphate dibasic anhydrous, and a stabilizer, such as hydroxymethyl cellulose, or hydroxypropyl methyl cellulose. When added to an aqueous solvent, the paraformaldehyde dissolves, and depolymerizes into a formaldehyde solution containing a stabilizer. The stabilized depolymerized formaldehyde solution is then ready for use, or can be modified by addition of other substances, such as sodium phosphate monobasic monohydrate.

According to still another aspect of the invention, a polymerized form of formaldehyde is available in granular form containing a polymerized form of formaldehyde, such as paraformaldehyde, a combination of buffers, such as sodium phosphate dibasic anhydrous and sodium hydroxide, and a stabilizer, such as hydroxymethyl cellulose, or hydroxypropyl methyl cellulose. When added to an aqueous solvent, the paraformaldehyde dissolves, and depolymerizes into a formaldehyde solution containing a stabilizer. The stabilized depolymerized formaldehyde solution is then ready for use, or can be modified by addition of other substances, such as sodium phosphate monobasic monohydrate.

In still other aspects, other fixatives, such as acetaldehyde, propionaldehyde, and other aldehydes can be prepared according to this invention. In general, any fixative that can be in a solid form under conditions of storage and use can be prepared using the methods of this invention.

BRIEF DESCRIPTION OF THE DRAWINGS

The invention will be described with respect to the particular embodiments thereof. Other objects, features, and advantages of the invention will become apparent with reference to the specification and drawings in which.

DETAILED DESCRIPTION

For explanation purposes, embodiments of the present invention will be described with respect to the aldehyde, formaldehyde, but it will be understood that other embodiments of the present invention may include other solid forms of polymerized aldehydes, other types of histological fixatives, and other reactive compounds. In general, embodiments of this invention include a dry preparation of an aldehyde or other reactive agent and a stabilizer.

Paraformaldehyde is a polymer that, upon de-polymerization can form formaldehyde. Polymer formation is one of the characteristic properties of the formaldehyde molecule. As indicated by the structures shown below, two fundamentally different polymer types for formaldehyde are possible.

(1)

(2)

Linear formaldehyde polymers, as illustrated by structure (1) are reversible polymers (i.e.: may be polymerized and de-polymerized) and react chemically as solid forms of formaldehyde. Representatives of structure (2) are encountered in polyhydroxyaldehydes.

Linear polymers range from the low molecular weight water-soluble oligo-oxymethylenes ("OOM") to the high molecular weight polyoxymethylenes ("POM"). Low molecular weight polymers, or OOMs, are typically obtained from an aqueous formaldehyde solution by a series of condensation or additive reactions involving methylene glycol. Low molecular weight polymers are brittle solids that depolymerize to produce formaldehyde in a form that is substantially free of water. High molecular weight polymers, or POMs, are generally produced by the polymerization of the anhydrous monomer or the cyclic trimer trioxane.

Commercial formaldehyde polymers typically include a mixture of linear polymers, such as $HO(CH_2O)_n.H$, the cyclic trimer $(CH_2O)_3$, trioxane and the POM or polyformaldehyde plastics also known as acetal resins of formaldehyde.

High molecular weight linear formaldehyde polymers generally include polyoxymethylene glycols ("POMG") and their derivatives. Polyoxymethylene glycols are hydrated polymers chemically and structurally related to methylene glycol. Although some of the POMGs may be isolated in comparatively pure state, POMGs are usually encountered as molecular weight mixtures, the formaldehyde content of which is a measure of the average degree of polymerization. On the basis of molecular weight, physical properties, and methods of preparation, POMGs may be classified into three groups: 1) the lower POMGs or oligo-oxymethylene glycols ("OOMG"), 2) paraformaldehyde and 3) alpha-polyoxymethylene. It is to be noted however that this classification is more or less arbitrary and is only made for purposes of convenience. The three groups merge into one another on the basis of degree of polymerization and absolute dividing lines cannot be drawn between them.

Figure 1:
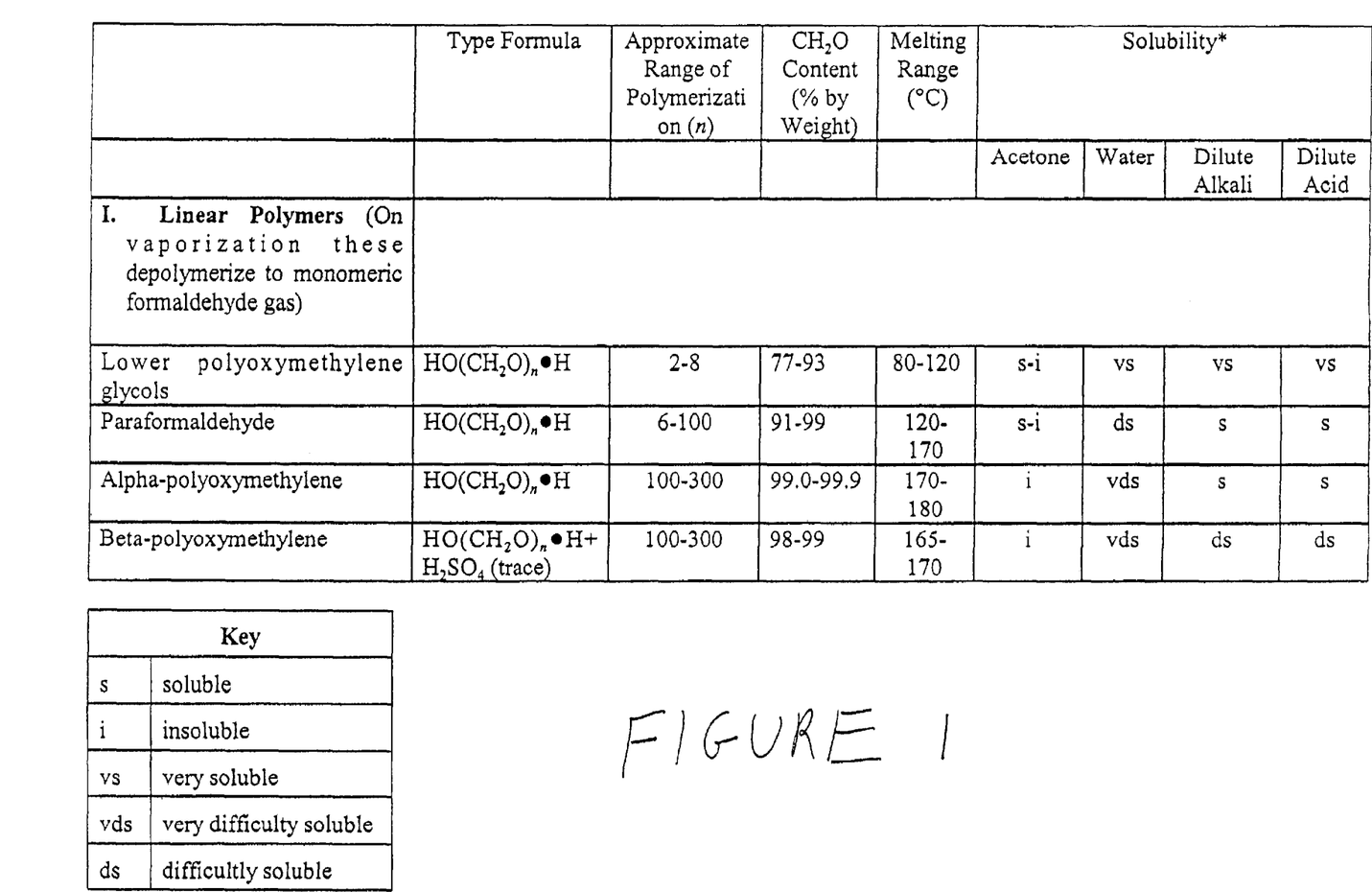
FIG. 1 is a table of some formaldehyde polymers.

In general, POMGs have the appearance of colorless powders possessing a characteristic odor of formaldehyde. POMGs properties such as melting point, solubility, chemical reactivity, etc., vary with molecular weight. As the degree of polymerization, indicated by n in the formula, $HO(CH_2O)_n.H$ increases, the formaldehyde content approaches 100% and the physical and chemical properties approach those of the polyoxymethylenes. FIG. 1 illustrates a table of some of the linear formaldehyde polymers.

When aqueous formaldehyde solutions containing from approximately 30% to approximately 80% formaldehyde are brought to room temperature or below, a precipitate consisting principally of the lower molecular weight POMG can be obtained. The point at which precipitation takes place can depend on the concentration of the formaldehyde solution, the temperature, the solvent, and/or the rate of cooling, among others.

The lower molecular weight POMGs, or OOMGs, are colorless solids melting in the range from about 80° C. to about 120° C. Polyoxymethylene glycols and OOMGs differ from paraformaldehyde and other higher homologs in being soluble in acetone and ether, and by dissolving with little or no decomposition. Polyoxymethylene glycols and OOMGs dissolve slowly in warm water with hydrolysis and/or other depolymerization reactions to form formaldehyde solutions. Polyoxymethylene glycols and OOMGs are insoluble in petroleum ether or other non-polar solvents.

Paraformaldehyde, as described herein, is a mixture of POMGs containing from about 90% to about 99% formaldehyde and a balance consisting principally of free and combined water. Polyoxymethylene glycols can contain from about 6 to about 100 formaldehyde units per molecule. The majority of the polyoxymethylene glycols in paraformaldehyde contain over 12 formaldehyde units per molecule. The chemical composition of paraformaldehyde can be expressed by the formula $HO(CH_2O)_n.H$. Common grades of paraformaldehyde include flaked and powdered materials having a minimum formaldehyde content of about 91% and powdered as well as granular grades having about a 95% minimum. Special grades of relatively high molecular weight paraformaldehyde may have a formaldehyde content of over 98%.

At ordinary temperatures, paraformaldehyde can gradually vaporize, and on long exposure to the atmosphere complete volatilization can eventually take place. Ultrasonic waves can also partially depolymerize paraformaldehyde. Sequential depolymerization can take place from the hydroxyl end of the molecule of paraformaldehyde as illustrated and described below.

The rate of depolymerization can depend on the number and availability of end groups. Thus, a high molecular weight polymer depolymerizes to formaldehyde more slowly than one of low molecular weight although the rate of the depolymerization can be the same for each. At the same time, the rate of depolymerization of a high molecular weight polymer, the end groups of which are at the outside of the polymer bundles, will differ from the rate of depolymerization of a high molecular weight polymer, the end groups of which are buried within a tangled mass of polymer chains.

As a result of such depolymerization mechanisms, liberation of water vapor from the polymer is a result of the chain degradation in which POMG breaks down to water and formaldehyde.

Paraformaldehyde dissolves in water, hydrolyzing and depolymerizing as it dissolves. The rate of depolymerization depends upon the temperature of the water. In general, at room temperature, it takes weeks at room temperature to depolymerize paraformaldehyde into formaldehyde within water. It takes even longer to depolymerize paraformaldehyde into formaldehyde in colder water. For example, a 28% formaldehyde solution may be obtained by agitating paraformaldehyde in water at about 18° C. for five weeks. Formaldehyde solutions obtained in this way are identical with those obtained by dissolving gaseous formaldehyde in water. It can be appreciated that the rate of depolymerization can increase in solutions at higher temperature. Any temperature can be used, but conveniently, temperatures below boiling are convenient. Such temperatures can be from room temperature to about 100° C. Hot water baths or double-boilers can be used in many settings, including laboratory or hospital settings.

It can be appreciated that under reflux conditions at elevated temperatures almost any desired concentration of formaldehyde can be obtained within a few hours. However, solutions obtained in this way are often cloudy due to incomplete depolymerization.

Figure 2:
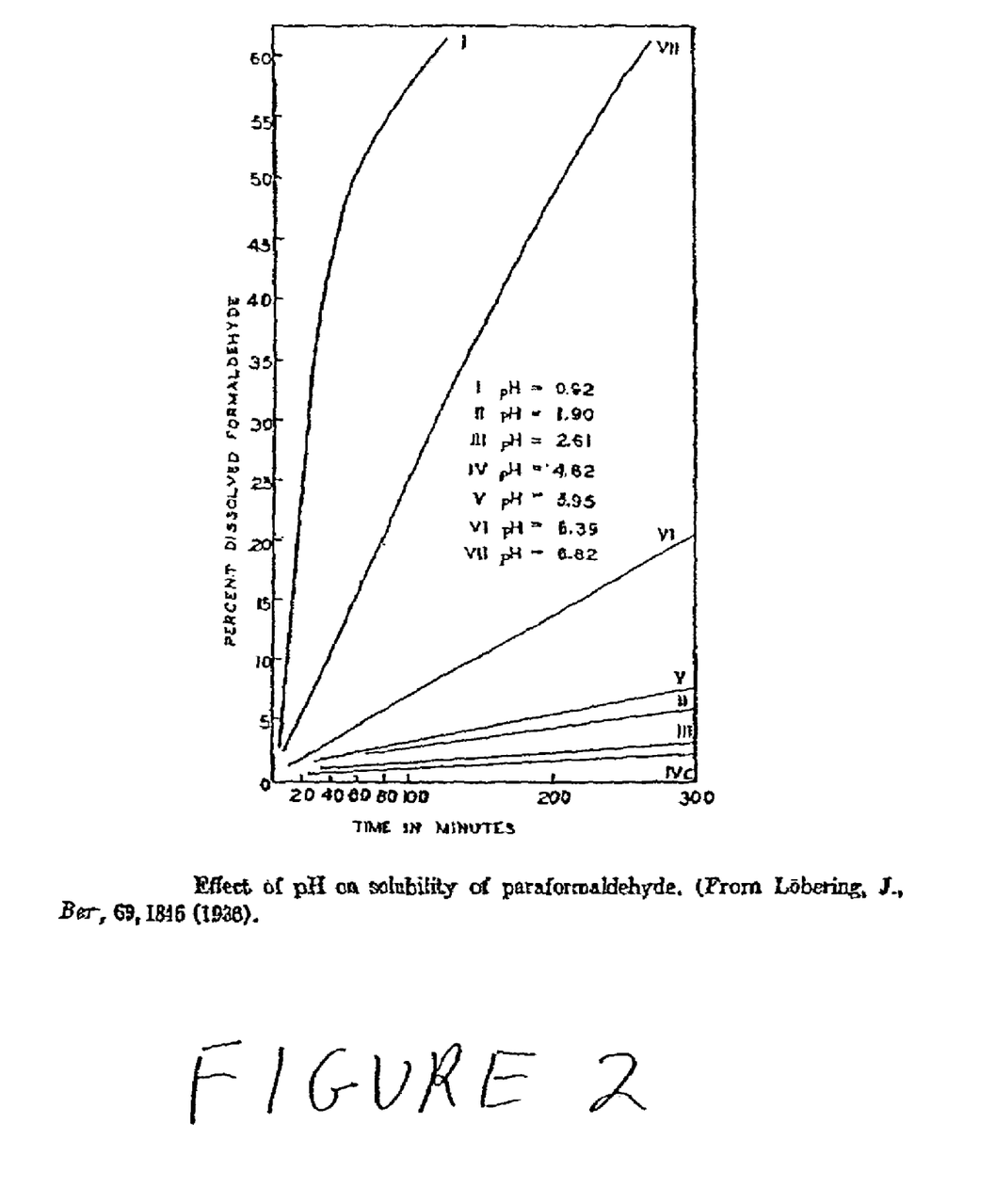
FIG. 2 is a graph which illustrates the effect of pH on aqueous solubility of paraformaldehyde.
Figure 3:
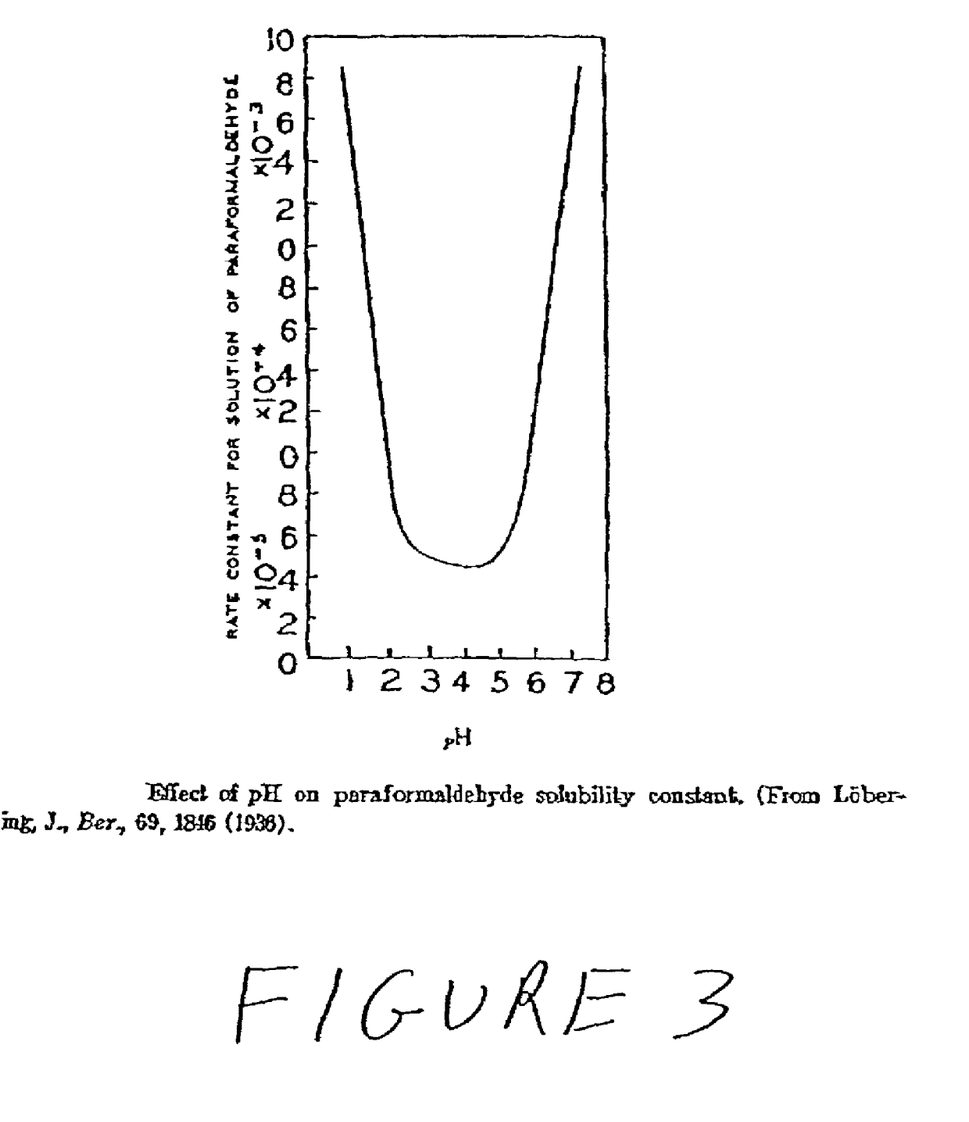
FIG. 3 is a graph which illustrates the effect of pH on paraformaldehyde aqueous solubility constant.

Depolymerization of polymeric formaldehyde can be influenced by pH. The hydrogen and hydroxide ion concentrations of the solution have a considerable influence on the rate of depolymerization. Depolymerization is at a minimum in the pH range of about 2.6 to about 4.3, and increases rapidly with higher or lower pH values as is illustrated in FIGS. 2 and 3. The rate of depolymerization can be increased more under alkaline conditions than acidic conditions, as hydroxyl ions can exert $10^7$ times stronger effects on depolymerization than hydrogen ions. At low temperatures, (e.g., about 25° C. and below) depolymerization of formaldehyde polymers is a slow reaction. Solutions in the pH range about 2.6 to about 4.3 require more than 50 hours to attain equilibrium after reduction of formaldehyde polymers from about 36.5% to about 3% at about 0° C. Methanol and similar substances that lower the ion product of water also lower the rate of depolymerization of polymeric formaldehyde.

In contrast to the relatively slow depolymerization in near-neutral conditions, dilute alkali and acids accelerate the rate of depolymerization of paraformaldehyde.

Measurements of the rate of depolymerization of paraformaldehyde in water show that at low concentrations of formaldehyde the reaction of depolymerization of paraformaldehyde is kinetically a monomolecular reaction. However, as the formaldehyde concentration increases, reverse reactions of a higher order occur, for example dissolved formaldehyde condenses and forms higher molecular weight homologs of polyoxymethylene glycols.

Mechanism of the hydrolytic depolymerization reactions of formaldehyde polymers differ under alkaline and acidic conditions. Under alkaline conditions, degradation proceeds in a stepwise fashion: formaldehyde units successively split from the ends of the linear POM molecule. Under acidic conditions, oxygen linkages within the molecular chain can be attacked by hydrogen ions, and large molecules can be split into smaller fragments.

The rate at which paraformaldehyde and other POMGs dissolve in water can reflect the degree of polymerization. Rate measurements of depolymerization of POMGs in water accordingly provide a useful method to compare the degree of polymerization of paraformaldehyde, alpha polyoxymethylene, and other polymers of this type.

An embodiment of the present invention provides a method for producing a solid mixture including a polymerized aldehyde, and at least one basic buffer which may be combined with an aqueous solution to form a solution containing a desirable concentration of the depolymerized aldehyde at an alkaline pH. A stabilizer may also be included in the original solid mixture or added to the solution to prevent the depolymerized aldehyde from repolymerizing.

Paraformaldehyde can be used to make compositions of this invention either "as is" from the manufacturer, or if desired, the material can be further pulverized to increase the surface area:volume ratio. Increasing the surface area:volume ratio can increase the speed with which polymerized paraformaldehyde depolymerizes. Furthermore, in dry-mixing processes, a pulverizer may be employed to decrease the size of particles of paraformaldehyde and/or buffer and/or stabilizer. Such pulverizers and methods for using them are known in the art and need not be described herein further.

The use of a first, basic member of a buffer pair (e.g., $PO_4^{-2}$, or $CO_3^{-2}$) can be especially useful because with such a member of a buffer pair, alkaline hydrolysis can be promoted, and then subsequently, when the desired degree of depolymerization is obtained, the second member of the buffer pair (e.g., $HOP_4^-$ and $HCO_3^-$, respectively) can be added to adjust the pH and the buffering capacity to within a desired working range.

Although buffers can be used that have any degree of hydration (e.g., coordinated with a certain number of moles of water per mole of buffer component), in some cases it can be desirable to use anhydrous buffers (e.g., those that contain no coordinated water molecules). Hydrated substances can liberate water to other components of the system, and the presence of water can result in partial depolymerization of paraformaldehyde, and therefore may liberate formaldehyde gas, which can be toxic.

Once the solution is formed, in an embodiment, a second solid buffer may be added to the solution to control the pH, osmolality, osmolarity, isotonic pressure of the solution, etc.

For example, one of the POM's, such as paraformaldehyde, may be combined with a solid alkaline buffer, such as sodium phosphate dibasic anhydrous. It can be desirable for the buffer material to have a relatively large surface area:volume ratio, to promote more rapid solubilization in aqueous media. When mixed with water at room temperature, the buffer produces a solution having a basic (alkaline) pH and the paraformaldehyde rapidly depolymerizes to a formaldehyde monomer. A stabilizer, such as hydroxypropyl methyl cellulose may also be included in the solid mixture or added after the solid mixture has been combined with water. The stabilizer will keep the formaldehyde from reversing back to paraformaldehyde.

In an alternative embodiment, more than one basic material may be included in the solid mixture. For example, in addition to the basic buffer sodium phosphate dibasic anhydrous, a second basic buffer, such as carbonate or a base such as sodium hydroxide may also be included. The inclusion of a second basic material, can further increase the rate of depolymerization of the aldehyde when combined with water. The addition of additional buffers also affects the pH value of the solution. Thus, to increase the pH of the solution, one can use a base, such as hydroxide ion, instead of using another member of a buffer pair (e.g., carbonate).

Other examples of materials which may be used individually or in combination include, but are not limited to, ammonium hydroxide, ammonium acetate, sodium acetate, lithium carbonate, lithium hydroxide, sodium bicarbonate, sodium carbonate, sodium citrate, and Tris (hydroxymethyl aminomethane) free base.

Stabilizers may be used to inhibit depolymerized aldehyde from repolymerizing. Stabilizers include, but are not limited to, hydroxymethyl cellulose, gelatin, pectin, carrageenan, polyoxymethylene ethers of higher fatty acids, hydrazine hydrate, hydroxylamine hydrochloride, and acidic nitrogen compounds (e.g., urea, melamine), and hydrogen sulfide.

If controlling the pH, osmolality, osmolarity, and isotonic pressure of the solution is desirable, a second member of the buffer pair, such as sodium phosphate monobasic monohydrate (for use with dibasic phosphate ions) may be added to the resultant solution. Alternatively, other buffers such as potassium phosphate monobasic ($KH_2PO_4$), sodium phosphate monobasic ($NaH_2PO_4$), and Tris (hydroxymethyl aminomethane) free base (HCl), or bicarbonate ($HCO_3^-$; used with carbonate ions $CO_3^{-2}$) may also be used to control pH, osmolality, osmolarity, and isotonic pressure.

The selection of a buffer for physiological or histological purposes can depend upon the pH to be desired of the final solution. Thus, buffer pairs can be selected that have a pK near the working pH. The pK of a buffer is the pH at which the concentrations of the buffer "base" (e.g., $PO_4^{-2}$) is equal to the buffer "acid" (e.g., $PO_4^-$). Buffering capacity (e.g., the ability to maintain pH in the face of increased acid or alkaline load) of a buffer solution is maximized when the concentrations of the buffer pairs are equal. Thus, in situations in which neutral solutions are desired (e.g., histological purposes), phosphate buffers can be desirable because the pK of a phosphate buffer system is about 6.8. However, one can use a buffer pair in a pH range within about 2 pH units so long as the concentration of the relevant acceptor of the pair is in sufficiently high free concentration to react with the acid or alkaline load. Numerous buffer pairs are known in the art and need not be described herein in detail.

In addition to using buffers, other materials may be included to adjust osmotic concentration of an aldehyde solution. For example, glucose, sucrose, mannitol, or salts (e.g., NaCl, KCl, etc) can be added. For fixation of biological samples, it can be desirable to use an isoosmolar solution (e.g., about 300 mOsm/L) or a slightly hyperosmolar solutions (e.g., slightly above about 300 mOsm/L). However, for fixation of other tissues, a more hyperosmolar solution can be used so long as the relationships between cells and tissues is not disrupted. For industrial uses, such as manufacture of plastics, concretes etc. the osmolarity of the solution can be selected as desired.

Figure 4:
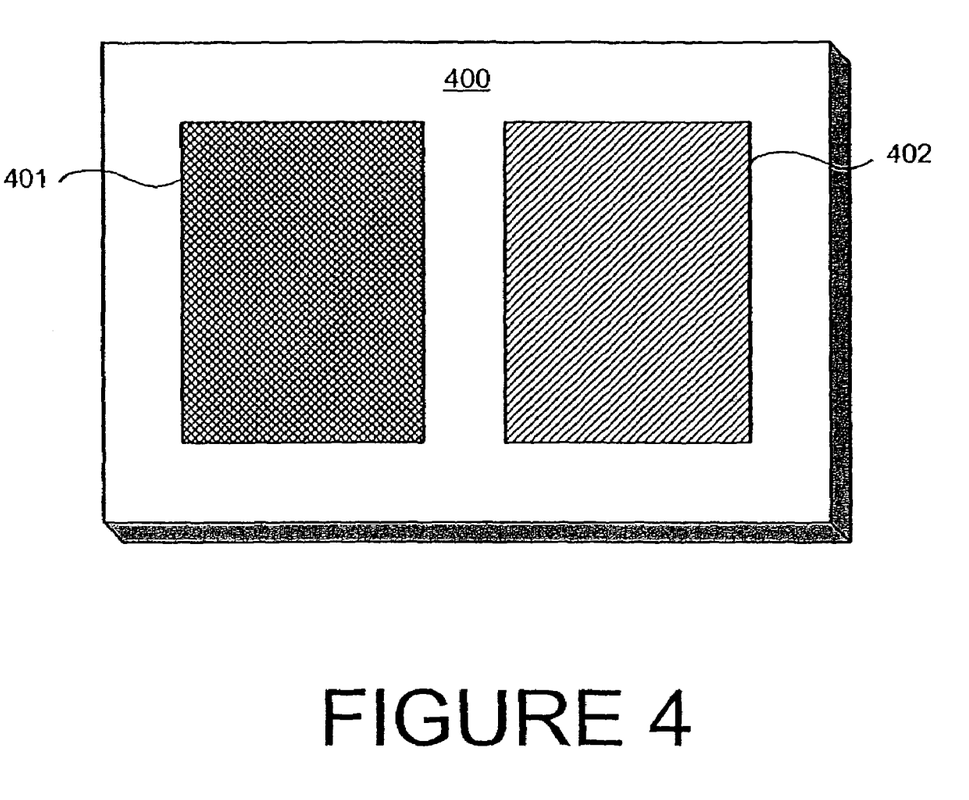
FIG. 4 illustrates a commercial embodiment of the present invention.

FIG. 4 illustrates an embodiment of the present invention which may be commercially distributed for producing a stabilized solution of formaldehyde. The embodiment described with respect to FIG. 4 may be used to easily produce one liter of a stabilized solution having a concentration of about 3.7% formaldehyde with a pH of about 6.85.

A kit 400 includes a first packet 401 containing a powdered mixture which includes approximately thirty-seven (37) grams of paraformaldehyde and approximately six and one half (6.5) grams of sodium phosphate dibasic anhydrous. A second packet 402 contains approximately four (4) grams of sodium phosphate monobasic monohydrate. Approximately 0.01 grams of hydroxypropyl methyl cellulose may be included in either packet as a stabilizer.

In producing a formaldehyde solution, the contents of the first packet 401 are mixed with one (1) liter of water, preferably at room temperature, and stirred until the powdered solution is dissolved. After mixing, a solution having a concentration of about 3.7% formaldehyde with a pH of about 10.5 is produced.

The contents of the second packet 402 may then be added and mixed until dissolved. The resulting solution has a concentration of about 3.7% formaldehyde and a pH of about 6.85. For histology purposes, the solution also has desirable osmolality, osmolarity, and isotonic pressure which protects tissue to be fixed with the solution.

In an alternative embodiment, the kit 400 may include more than one buffer in the first packet 401 thereby further effecting the rate of depolymerization and pH when combined with water. For example, and again describing the kit 400 for use in producing one (1.0) liter of stabilized solution, the powdered mixture of the first packet 401 includes approximately thirty-seven (37) grams of paraformaldehyde, approximately four (4.0) grams of sodium phosphate dibasic anhydrous, and approximately one (1.0) gram of sodium hydroxide. A second packet 402 contains approximately six and one half (6.5) grams of sodium phosphate monobasic monohydrate. Approximately 0.01 grams of hydroxypropyl methyl cellulose may be included in either packet as a stabilizer.

As described above, in producing a formaldehyde solution, the contents of the first packet 401 are mixed with one (1) liter of water, preferably at room temperature, and stirred until the powdered solution is dissolved. The addition of sodium hydroxide in the first packet 401 increases the rate at which the powdered solution is dissolved and increases the pH of the resulting solution. After mixing, a solution having a concentration of about 3.7% formaldehyde with a pH of about 11.2 is produced.

The contents of the second packet 402 may then be added and mixed until dissolved. The resulting solution has a concentration of about 3.7% formaldehyde and a pH of about 7.15. For histology purposes, the solution also has desirable osmolality, osmolarity, and isotonic pressure which protects tissue to be fixed with the solution.

The kit 400 may be safely shipped, stored, and later combined with water to form a solution of about 3.7% formaldehyde which contains no chemical contaminants, such as methanol.

It will be understood that the above examples are for explanation purposes only, and other solid forms of polymerized aldehydes, buffers, and/or stabilizers may be used at different amounts and/or ratios. Additionally, kit 400 may contain other amounts and/or ratios than those described above which may mixed with different amounts of water to produce larger or smaller amounts of a formaldehyde solution at different concentrations.

Embodiments of the above described invention have several advantages over current techniques of producing, transporting and storing aldehyde solutions. Transporting a powdered substance, which may be safely and easily mixed with water by an end user after delivery, requires less space, is lighter (approximately twenty (20) times lighter than an aqueous solution of 37% paraformaldehyde), cheaper, and much safer to transport than the current practice of manufacturing a liquid aldehyde solution and then shipping the liquid solution to the end user. Additionally, a user can order a much larger quantity of the powdered substance and safely store it for an extended period of time, and in a reduced amount of space, as compared to the amount of space required to store the liquid solution.

It can be appreciated that other aldehydes can be prepared using the same principles described herein. In general, any aldehyde that is solid under the physical conditions of preparation and storage can be subject to the methods of this invention. Examples of such suitable aldehydes include proprionaldehyde and acetaldehyde. Although glutaraldehyde and butyraldehyde may be liquids under certain conditions, they may be prepared using the teachings of this invention.

Moreover, in addition to aldehydes, other fixatives may be prepared, stored and transported using the methods of this invention. Thus, osmium tetraoxide, picric acid, potassium dichromate, mercuric chloride, potassium permanganate, and acrolein can be conveniently prepared according to this invention.

Any suitable buffer may be used to prepare the compositions of this invention. For many purposes, phosphate buffers or TRIS may be used.

In addition to buffers, one or more stabilizers may be used. Stabilizers include carboxypolysaccharides, by way of example, carboxymethylcellulose (CMC), hydroxymethylcellulose (HMC) and numerous other cellulose derivatives, as well as alginates, hyaluronates and the like. Proteins can also be used as stabilizers, and include byway of example, gelatin. Additionally, pectin, carageenan, fatty acid ethers, hydrazine, hydroxylurea, urea, melamine and other acidic nitrogen-containing compounds, and hydrogen sulfide can also be used. It can be appreciated that other compounds having similar properties can be used in a composition of this invention as a stabilizer.

If desired, the above mixtures can be prepared in dried form and stored in a packet. Packets are convenient to store and weigh less than solutions containing the same amounts of reactive agent, buffer and/or stabilizer. Thus, great savings of space, weight, transportation costs, as well as increased safety can be achieved using powdered forms. In other embodiments, preparations can comprise two packets, in which a first packet contains a fixative and a buffer, and a second packet contains a powdered form of a stabilizer. Upon dissolving the first packet, a solution of a fixative in a buffer is obtained. In other embodiments, a first packet can contain a fixative and a stabilizer in granular form, and a second packet contains a buffer material, that upon dissolving in aqueous solution, results in formation of a buffer solution having a desired pH and osmolarity.

It can be appreciated that after dissolution the contents of the packets and mixing them together, the osmolarity can be further adjusted to a desired value, for example, 300 mOsm/L. It can also be appreciated that agents that contribute to osmotic pressure can be included along with fixative, buffer, and/or stabilizer packets. Thus, it is convenient if the osmotic agent selected is also granular or powdered, and can dissolve relatively rapidly in aqueous medium. Many such osmotic agents are known in the art, but include sucrose and other sugars, salts, such as NaCl and the like, numerous other small molecules, as well as large molecules, such as proteins, complex carbohydrates and the like. By adjusting the amounts of dry materials in a packet and by pre-selecting the amount of aqueous medium added, the concentration, pH, osmolarity and/or other characteristic of a solution can be obtained.

It can also be appreciated that a first packet may contain a powdered or granular fixative and a second packet may contain an additional buffer and/or stabilizer and/or osmotic agent. It is well known in the art to prepare various buffers as powders. By selecting the amounts of buffer pairs (e.g., sodium phosphate monobasic and sodium phosphate dibasic), the concentration and pH of the resulting solution can be achieved without the necessity of adjusting the pH after making the solution. Thus, use of the powdered formulations of this invention can be very convenient to use, in particular if large amounts of materials are used (e.g., as in industrial manufacturing applications).

Compositions of this invention are conveniently manufactured and transported as kits. A kit can contain a first packet containing powdered fixative (optionally, with buffer and/or stabilizer), a second packet (e.g., containing stabilizer and/or buffer and/or second buffer, and/or osmotic agent), and instructions for preparing liquid solutions. Optionally, a kit may contain measuring devices, cups, flasks, pipettes, and/or other equipment routinely used for making fixative solutions.

Uses of Powdered Compositions

In certain embodiments, powdered formalin or other histological fixatives find use in histology and other medically related fields. Thus, certain aldehydes, picric acid, dichromates, permanganates and like materials can be used for light microscopy, for example for hospital or clinical laboratory diagnostic procedures. Additionally, certain other fixatives, including permanganates, dichromates, osmium tetroxide, uranyl acetate and the like may conveniently be used for electron microscopic purposes, including medical diagnosis, laboratory research and the like. In other embodiments, one or more of these heavy metal materials can be prepared as a second packet.

In addition, in other embodiments, compositions and methods of this invention can be suitably used for any industrial purpose in which a reactant, such as an aldehyde is used. For example, numerous uses of formaldehyde are know in the art and are included in *Formaldehyde,* Third Edition, J. Frederic Walker, Reinhold Publishing Corporation, New York, 1964, incorporated herein fully by reference, in particular, Chapter 20, pp 552–660. A brief list of industries and/or uses of formaldehyde preparations of this invention includes manufacture of acetal resins, agriculture, analysis, catalysts, concrete, plaster and related products, cosmetics, deodorization, disinfection and fumigation, dyes and dye-house chemicals, embalming and preserving, explosives, fireproofing, fuels, gas absorbents, hydrocarbon products, insecticides, leather, fur and hair products, medicine, metal manufacturing, paper, photography, protein modification, rubber, solvents and plasticizers, stabilizers, starch, surface active agents (e.g., detergents), textiles and wood products.

Agricultural uses include formulation of slow release nitrogen fertilizers and for controlling microorganisms responsible for plant diseases. Analytical uses include both quantitative and qualitative analysis of amino acid composition of proteins, analysis of nitrates, halogen acids, inorganic halides, alkali cyanides and numerous other nitrogen-containing materials, heavy metals, including gold, silver copper and bismuth. Catalytic uses include preparation of hydrocarbons, alcohols and other products of hydrogenation. Additional uses include manufacture of cement and other concrete products and plaster. Formalin is also a deodorant, and has uses in mouthwashes, soaps and germicides, used alone or with phenols. Formaldehyde can react with ammonia, amines, hydrogen sulfide, mercaptans and other materials that have strong and/or offensive odors. Aldehydes can cross-link proteins together, and thus, can destroy bacteria, fungi, molds and yeasts. Formaldehyde is widely used as an embalming agent and for preserving tissues for later study. As indicated above, powdered formaldehyde preparations of this invention find wide use in hospitals and laboratories. Formaldehyde also finds significant use in the manufacture of explosives, where the aldehyde can be reacted with nitrogen-containing or oxygen-containing compounds to form materials that can liberate a large amount of energy upon detonation. In some cases, formaldehyde can be used to stabilize what would otherwise be unstable explosives. In the petroleum industries, formaldehyde finds use in drilling and operation of oil wells, in purification, modification and refining of petroleum fractions and the synthesis of antioxidants. In the leather and hide industries, formaldehyde is widely used in tanning and in preparation of hair products for felting and dyeing. In the metal industries, formaldehyde can be used as acid inhibitors, reducing agents and electroplating agents.

It should be understood that the particular embodiments described above are only illustrative of the principles of the present invention, and various modifications could be made by those skilled in the art without departing from the scope and spirit of the invention. Thus, the scope of the present invention is limited only by the claims that follow:

INDUSTRIAL APPLICABILITY

Embodiments of powdered formulations of aldehydes find use at least in industries involving agriculture, analysis, catalysts, concrete, plaster and related products, cosmetics, deodorization, disinfection and fumigation, dyes and dye-house chemicals, embalming and preserving, explosives, fireproofing, fuels, gas absorbents, hydrocarbon products, insecticides, leather, fur and hair products, medicine, metal manufacturing, paper, photography, protein modification, rubber, solvents and plasticizers, stabilizers, starch, surface active agents, textiles or wood products.

What is claimed is:

1. A kit for producing a stabilized solution of an aldehyde, the kit comprising:
   a first packet including a solid form of a polymerized aldehyde and a first solid basic buffer;
   a second packet including a second solid basic buffer; and
   wherein said first solid basic buffer is sodium phosphate dibasic anhydrous and said second solid basic buffer is sodium phosphate monobasic monohydrate.

2. A kit for producing a stabilized solution of an aldehyde, the kit comprising:
   a first packet including a solid form of a polymerized aldehyde and a first solid basic buffer;
   a second packet including a second solid basic buffer; and
   wherein said first packet further includes a solid stabilizer.

3. The kit of claim 2, wherein said solid stabilizer is hydroxypropyl methyl cellulose.

4. A kit for producing a stabilized solution of an aldehyde, the kit comprising:
   a first packet including a solid form of a polymerized aldehyde and a first solid basic buffer;
   a second packet including a second solid basic buffer; and
   wherein said second packet further includes a solid stabilizer.

5. The kit of claim 4, wherein said stabilizer is hydroxypropyl methyl cellulose.

6. A kit for producing one liter of a stabilized solution of formaldehyde when combined with an aqueous solvent, the kit comprising:
   a first packet including:
      approximately 37.0 grams of paraformaldehyde;
      approximately 4.0 grams of sodium phosphate dibasic anhydrous;
      approximately 1.0 gram of sodium hydroxide; and,
      approximately 0.01 grams of hydroxypropyl methyl cellulose; and
   a second packet including approximately 6.5 grams of sodium phosphate monobasic monohydrate.

7. A method for producing a solution of aldehyde, the method comprising the steps of:
   providing a first amount of an aqueous solvent;
   combining a second amount of a polymerized aldehyde and a third amount of a first basic buffer with said aqueous solvent; and,
   combining a fourth amount of a second basic buffer with said aqueous solvent, wherein said step of combining a second amount of a polymerized aldehyde and a third amount of a first basic buffer with said aqueous solvent, further includes the step of combining a third basic buffer with said aqueous solvent.

8. The method of claim 7, wherein said third basic buffer is sodium hydroxide.

9. The method of claim 7, wherein said aqueous solvent is water.

10. The method of claim 7, wherein said solution of aldehyde is a solution of formaldehyde, and said polymerized aldehyde is paraformaldehyde.

11. The method of claim 7, wherein said first basic buffer is sodium phosphate dibasic anhydrous.

12. The method of claim 7, wherein said second basic buffer is sodium phosphate monobasic monohydrate.

13. A kit comprising:
   packet containing powdered formaldehyde and a stabilizer;
   a second packet containing a buffer material; and
   instructions for reconstituting an aqueous formaldehyde solution;
   wherein said stabilizer is selected from the group consisting of carboxypolysaccharides, proteins, fatty acid ethers, acidic nitrogen compounds, carageenan, hydroxylamine and hydrogen sulfide.

14. A kit comprising:
   a first packet containing a powdered fixative and a stabilizer;
   a second packet containing a buffer material; and
   instructions for reconstituting a solution of said fixative;
   wherein the kit further includes another fixative.

15. A kit comprising:
   a first packet containing a powdered fixative and a stabilizer;
   a second packet containing a buffer material; and
   instructions for reconstituting a solution of said fixative;
   wherein said fixative is selected from the group consisting of an aldehyde, picric acid, osmium tetraoxide, uranyl acetate, a dichromate, a permanganate, mercuric chloride and acrolein.

* * * * *

UNITED STATES PATENT AND TRADEMARK OFFICE
CERTIFICATE OF CORRECTION

PATENT NO. : 7,204,959 B2 Page 1 of 1
APPLICATION NO. : 10/357596
DATED : April 17, 2007
INVENTOR(S) : J.L. Biesecker It is certified that error appears in the above-identified patent and that said Letters Patent is hereby corrected as shown below:

| COLUMN | LINE | ERROR |
|---|---|---|
| 12 (Claim 13, | 37 line 2) | "packet containing" should read --a first packet containing-- |

Signed and Sealed this

Fourteenth Day of August, 2007

JON W. DUDAS
*Director of the United States Patent and Trademark Office*